(12) United States Patent
Donofrio

(10) Patent No.: US 8,165,676 B2
(45) Date of Patent: Apr. 24, 2012

(54) OPTICAL SENSOR AND METHOD FOR DETECTING A PATIENT CONDITION

(75) Inventor: William T. Donofrio, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 467 days.

(21) Appl. No.: 11/962,745

(22) Filed: Dec. 21, 2007

(65) Prior Publication Data

US 2009/0163968 A1   Jun. 25, 2009

(51) Int. Cl.
*A61B 5/0432* (2006.01)
(52) U.S. Cl. ......... 607/19; 600/301; 600/322; 600/324; 600/500; 607/3; 607/6; 607/18
(58) Field of Classification Search ............ 607/6, 3, 607/17–22; 600/310–333, 542, 544, 500–502, 600/301
See application file for complete search history.

(56) References Cited

U.S. PATENT DOCUMENTS

| | | | |
|---|---|---|---|
| 3,985,449 A | 10/1976 | Patrin et al. | |
| 4,100,562 A | 7/1978 | Sugawara et al. | |
| 4,202,339 A | 5/1980 | Wirtzfeld et al. | |
| 4,467,807 A | 8/1984 | Bornzin | |
| 4,730,389 A | 3/1988 | Baudino et al. | |
| 5,010,381 A | 4/1991 | Shiba et al. | |
| 5,144,381 A | 9/1992 | Furnyama et al. | |
| 5,902,326 A | 5/1999 | Lessar et al. | |
| 6,122,536 A | 9/2000 | Sun et al. | |
| 6,125,290 A | 9/2000 | Miesel et al. | |
| 6,198,952 B1 | 3/2001 | Miesel et al. | |
| 2002/0026108 A1* | 2/2002 | Colvin, Jr. | 600/316 |
| 2004/0039269 A1 | 2/2004 | Ward et al. | |
| 2004/0176669 A1 | 9/2004 | Colvin et al. | |
| 2004/0220629 A1 | 11/2004 | Kamath et al. | |
| 2007/0015981 A1* | 1/2007 | Benaron et al. | 600/323 |
| 2007/0156085 A1 | 7/2007 | Schulhauser et al. | |
| 2007/0239215 A1 | 10/2007 | Bhunia et al. | |
| 2007/0255148 A1* | 11/2007 | Bhunia | 600/509 |
| 2008/0208020 A1 | 8/2008 | Cinbis et al. | |

FOREIGN PATENT DOCUMENTS

| | | |
|---|---|---|
| WO | 2004091719 | 10/2004 |
| WO | 2006113394 | 10/2006 |

OTHER PUBLICATIONS

International Search Report, PCT/US2008/084657, 7 pages.

* cited by examiner

*Primary Examiner* — Niketa Patel
*Assistant Examiner* — Rex R Holmes
(74) *Attorney, Agent, or Firm* — Michael C. Soldner

(57) ABSTRACT

An implantable medical device for monitoring tissue perfusion that includes a light source emitting light having a light wavelength corresponding to a blue to ultraviolet light spectrum and a light detector receiving light emitted by the light source and scattered by a volume of body tissue. The light detector emits a signal correlated to the received light wavelength, and a processor receives the signal from the light detector and determines a patient condition in response to the signal.

16 Claims, 9 Drawing Sheets

OPTICAL SENSOR AND METHOD FOR DETECTING A PATIENT CONDITION

TECHNICAL FIELD

The invention relates generally to implantable medical devices and, in particular, to an implantable optical sensor for use in a medical device system for detecting a patient condition.

BACKGROUND

Implantable medical devices (IMDs) for monitoring a physiological condition or delivering a therapy typically include one or more physiological sensors. Physiological sensors used in conjunction with an IMD provide a signal related to a physiological condition from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors are employed in IMDs as physiological sensors configured to detect changes in light modulation by a body fluid or tissue measurement volume due to a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
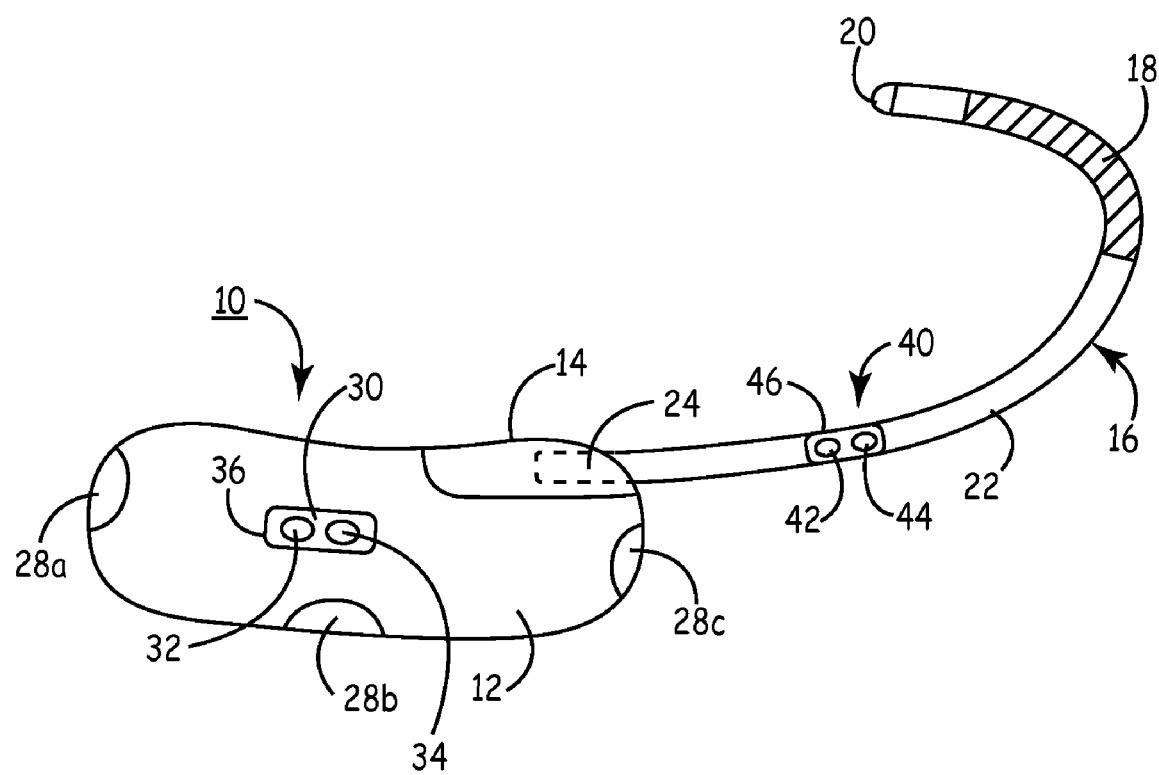
FIG. 1 is an illustration of one IMD configuration in which an optical sensor and associated method for determining a patient condition may be implemented.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is an illustration of one IMD configuration in which an optical sensor and associated method for determining a patient condition may be implemented. The IMD is shown embodied as a subcutaneous implantable cardioverter defibrillator (SubQ ICD) 10. SubQ ICD 10 includes a housing 12 with a connector 14 for attaching a subcutaneous sensing and cardioversion/defibrillation therapy delivery lead 16.

Subcutaneous lead 16 includes of a distal defibrillation coil electrode 18, a distal sensing electrode 20, an insulated flexible lead body 22 and a proximal connector pin 24 for connection to SubQ ICD 10 via connector 14. SubQ ICD 10 further includes multiple electrodes 28a, 28b, and 28c, incorporated along housing 12 and referred to collectively as subcutaneous electrode array (SEA) 28. SEA 28 is shown welded into place on the periphery of the housing of SubQ ICD 10 and is connected via wires to electronic circuitry within housing 12. SEA 28 shown in FIG. 1 includes three electrodes 28a, 28b and 28c positioned to form orthogonal signal vectors though other embodiments may include any number of subcutaneous housing-based electrodes. Any of the electrodes included in SEA 28 or on subcutaneous lead 16 may be selected in any combination for sensing subcutaneous ECG signals for use in monitoring a patient's heart rhythm and synchronizing anti-arrhythmia therapies.

According to embodiments of the present invention, SubQ ICD 10 further includes a tissue perfusion sensor (TPS) 30. TPS 30 is assembled within housing 12 along a window 36 formed in housing 12. TPS 30 is an optical sensor including a light emitting portion 32 and a light detecting portion 34. As will be described in detail herein, light emitting portion 32 emits light through window 36. The emitted light is scattered by an adjacent tissue volume in contact with SubQ ICD 10 at the implant site. Light detecting portion 34 detects the scattered light incident on detecting portion 34 and generates a signal responsive to changes in the intensity of the incident light. The light wavelengths detected by detecting portion 34 are selected to correlate to a physiological condition in the tissue associated with changes in tissue perfusion. The TPS signal is used by SubQ ICD 10 in detecting or confirming a cardiac condition, which in turn may trigger the delivery of an anti-arrhythmia therapy, such as a defibrillation shock, by SubQ ICD 10.

Additionally or alternatively, a TPS 40 may be carried by subcutaneous lead 16. TPS 40 is assembled within lead body 22 along a window 46 formed in the lead body 22. Control signals for causing a light source within light emitting portion 42 are generated by SubQ ICD 10 and transmitted to light emitting portion 42 along a conductor (not shown) carried by lead 16. Light is emitted through window 46 from light emitting portion 42. The emitted light is scattered by an adjacent tissue volume, and scattered light is detected by light detecting portion 44. A signal generated by light detecting portion 44 is transmitted SubQ ICD 10 along a conductor (not shown) carried by lead 16.

The signals generated by TPS 30 and 40 are responsive to physiological changes in the targeted tissue volume corresponding to the perfusion of the targeted tissue. In particular, the light wavelengths detected by TPS 30 and TPS 40 may correspond to the degree of oxygenation of the targeted tissue volume, which will decrease when tissue perfusion is compromised. Accordingly, as used herein, "tissue perfusion sensor" refers to an optical sensor used for detecting physiological changes in a targeted tissue volume correlated to a change in the perfusion of the tissue volume.

Figure 2:
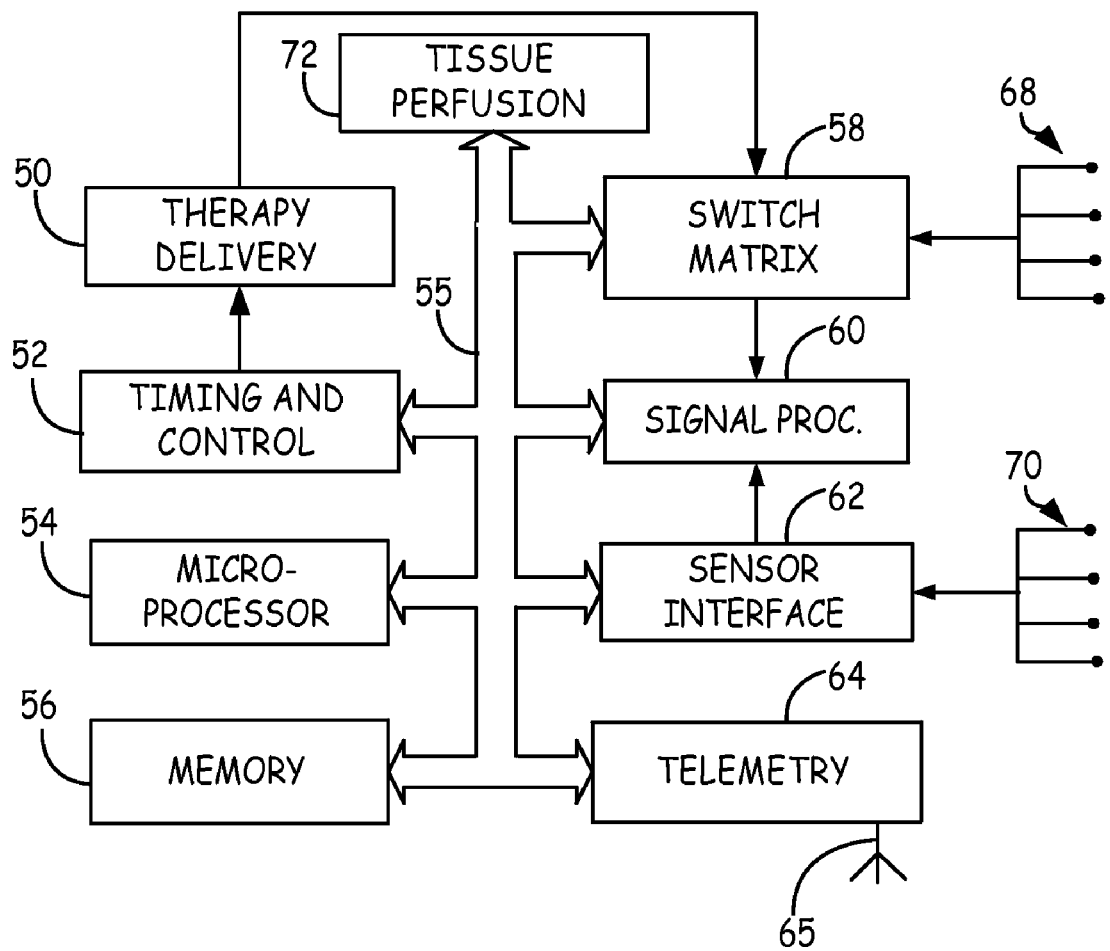
FIG. 2 is a functional block diagram of a SubQ ICD, such as the SubQ ICD shown in FIG. 1.

FIG. 2 is a functional block diagram of a SubQ ICD, such as SubQ ICD 10 shown in FIG. 1. SubQ ICD 10, referred to hereafter as "ICD 10", generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of ICD 10 via a data/address bus 55. ICD 10 includes therapy delivery module 50 for delivering cardioversion/defibrillation shocks and optionally other cardiac pacing therapies or arrhythmia therapies, under the control of timing and control 152. Therapy delivery unit 150 is typically coupled to two or more electrode terminals 68 via a switch matrix 58. Switch matrix 58 is used for selecting which electrodes and corresponding polarities are used for delivering electrical stimulation pulses. Terminals 68 may be coupled to connectors providing electrical connection to SEA 28 and lead-based electrodes 18 and 20, shown in FIG. 1.

Electrode terminals 68 are also used for receiving cardiac electrical signals. Cardiac electrical signals are sensed for determining when an electrical stimulation therapy is needed and may be used in controlling a stimulation mode and the timing of electrical stimulation pulses, including CV/DF shocks. Electrodes used for sensing and electrodes used for stimulation may be selected via switch matrix 58. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. Signal processing circuitry 60 may include event detection circuitry, e.g. R-wave detection circuitry, commonly used by implantable pacemakers and ICDs.

Arrhythmia detection algorithms may be implemented for detecting ventricular tachycardia (VT), ventricular fibrillation (VF) as well as atrial arrhythmias such as atrial fibrillation (A FIB). Ventricular event intervals (R-R intervals) sensed from the EGM signals are commonly used for detecting ventricular arrhythmias. In response to an arrhythmia detection, a programmed arrhythmia therapy is delivered by therapy deliver module 50 under the control of timing and control 52.

ICD 10 is additionally coupled to one or more physiological sensors via physiological sensor terminals 70. Physiological sensors may include pressure sensors, accelerometers, flow sensors, blood chemistry sensors, activity sensors or other physiological sensors known for use with implantable cardiac stimulation devices. Physiological sensors may be carried by leads extending from ICD 10 or incorporated in or on the ICD housing. In addition or alternatively to detecting an arrhythmia using cardiac electrical signals, other physiological signals may be relied upon for detecting and/or confirming the presence of an arrhythmia. In particular, sensor terminals 70 provide connection to a tissue perfusion sensor, which may be TPS 30 incorporated along the housing 12 of ICD 10 or TPS 40 carried by subcutaneous lead 16 as shown in FIG. 1.

Signals received at sensor terminals 70 are received by a sensor interface 62 which provides sensor signals to signal processing circuitry 60. Sensor signals are used by microprocessor 54 for detecting physiological events or conditions. In particular signals from a TPS 30 or 40 are received for determining changes in tissue perfusion, which can be an indication of insufficient cardiac output due to a cardiac arrhythmia or another hemodynamic or respiratory insufficiency. A tissue perfusion module 72 may be implemented for receiving TPS signals from sensor interface 62 or a signal processor 60. Tissue perfusion module 72 is configured to execute algorithms for determining a relative change or level of tissue perfusion using the TPS sensor and provides microprocessor 54 with tissue perfusion information. The tissue perfusion data may be used for determining the need for delivering a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. A tissue perfusion monitoring algorithm may be stored in memory 56 and executed by microprocessor 54 with input received from electrode terminals 68 and/or sensor terminals 70 for detecting a change in tissue perfusion. Alternatively, tissue perfusion monitor 72 may be embodied as dedicated circuitry for receiving TPS signals for generating a signal indicating a change or relative level of tissue perfusion. As will be described below, timing and control 52 may respond to the tissue perfusion data by altering a pacing mode, pacing parameter, arrhythmia detection parameter, and/or arrhythmia therapy according to perfusion response data stored in memory 56. Data relating to tissue perfusion may be stored in memory 56 for later retrieval.

ICD 10 further includes telemetry circuitry 64 and antenna 65. Programming commands or data are transmitted during uplink or downlink telemetry between ICD telemetry circuitry 64 and external telemetry circuitry included in a programmer or monitoring unit. Telemetry circuitry 64 and antenna 65 may correspond to telemetry systems known in the art.

Figure 3A:
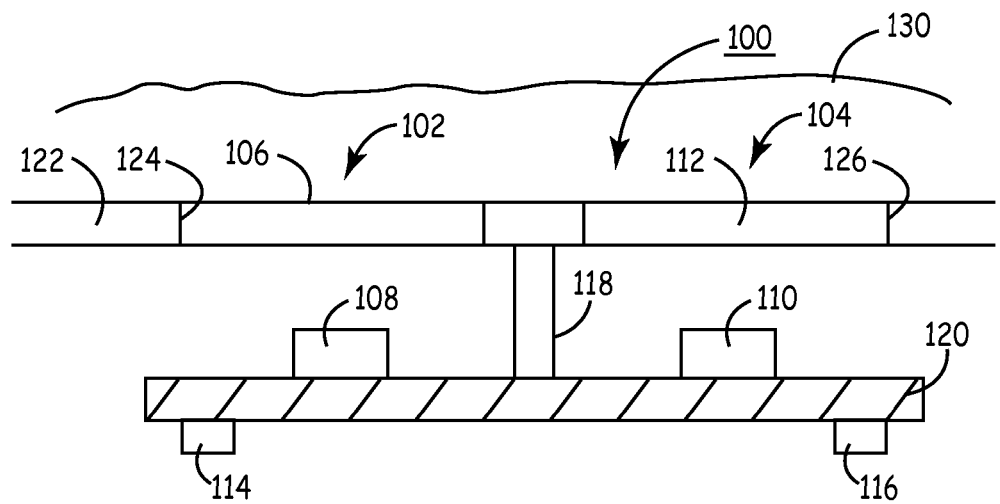
FIG. 3A is a schematic diagram of a tissue perfusion sensor (TPS) according to one embodiment of the present invention.

FIG. 3A is a schematic diagram of a TPS according to one embodiment of the present invention. TPS 100 shown in FIG. 3A and in other TPS configurations described herein may be implemented in an implantable medical lead or in the housing an implantable electronic device, such as subcutaneous ICD 10 or any other implantable pacemaker, ICD, neurostimulator, monitoring device, drug pump, or the like. TPS 100 includes a light emitting portion 102 and a light detecting portion 104. Light emitting portion 102 includes a light source 108 mounted on a circuit board 120 which enables electrical coupling to integrated circuitry 114 for delivering driver signals to light source 108. Light emitted by light source 108 in response to driver signals provided by integrated circuitry 114 passes through lens 106 mounted within a window 124 formed in housing 122. Housing 122 corresponds to an outer housing, capsule, or insulation in which TPS 100 is implemented, such as SubQ ICD housing 12 or lead body 22 shown in FIG. 1. In some embodiments, a ferrule (not shown) may be used for mounting lens 106 in housing 122. Reference is made, for example, to U.S. Pat. No. 5,902, 326 (Lessar, et al.), hereby incorporated herein by reference in its entirety.

Light detecting portion 104 includes a light detecting component 110, also referred to herein as a "light detector", mounted on circuit board 120 and electrically coupled to integrated circuitry 116 which receives the current emitted by light detecting component 110 in response to scattered light incident on detecting component 110. Integrated circuitry 116 provides the light detecting component signal to processing circuitry, such as microprocessor 54 or tissue perfusion monitor 72 shown in FIG. 2, configured to perform an algorithm for detecting a change in a tissue perfusion using the signal. Integrated circuitry 116 may include an analog-to-digital converter and flash memory for digitizing the analog signal and providing the digitized signal to processing circuitry.

Circuit board 120 is shown as a single circuit board on which both emitting portion 102 and detecting portion 104 are assembled. In alternative embodiments, separate circuit boards may be provided for each emitting and detecting portion. Emitting portion 102 and detecting portion 130 are separated by a light barrier 118 to prevent light emitted from light source 108 from being received directly by light detecting component 110. Light emitted from emitting portion 102 is scattered by an adjacent tissue volume 130. Scattered light passes through lens 112 mounted in window 126 of housing 122. Lenses 106 and 112 are commonly formed from sapphire.

Light source 108 is embodied as any opto-electronic component capable of emitting light in response to an applied current or voltage. For the purposes of monitoring tissue perfusion, it is desirable to detect a condition of substantially deoxygenated tissue in some applications. The detection of blue light scattered by a targeted tissue volume is effective in detecting a state of deoxygenation. Accordingly, light source 108 is capable of emitting light having a wavelength falling into the blue to ultraviolet light spectrum. Light source may emit light corresponding to other wavelengths in some embodiments. For example, light source 108 may be embodied as a white light source in some embodiments which includes a broad spectrum of light wavelengths. In another embodiment light source 108 is a light emitting diode (LED) capable of emitting a narrow band or targeted light wavelength, e.g., an LED emitting light substantially corresponding to blue, violet or ultraviolet light wavelengths.

Light detecting component 110 is embodied as any opto-electronic component capable of emitting current in the presence of light. Examples of light detecting components include photodetectors, photoresistors or light dependent resistors, photodiodes, phototransistors, photovoltaic cells, or charge-coupled devices. Light detecting component 110 is at least capable of emitting a current in response to incident light falling in the blue to ultraviolet light spectrum and may be responsive to other light wavelengths.

In one embodiment light detecting component 110 is embodied as a photodetector and light source 108 is embodied as a blue light LED. Blue light emitted by source 108 and scattered by tissue volume 130 is detected by light detecting component 110. A signal generated by TPS 100 will be correlated to a state of deoxygenation of tissue volume 130 and used for determining a metric of tissue perfusion.

Figure 3B:
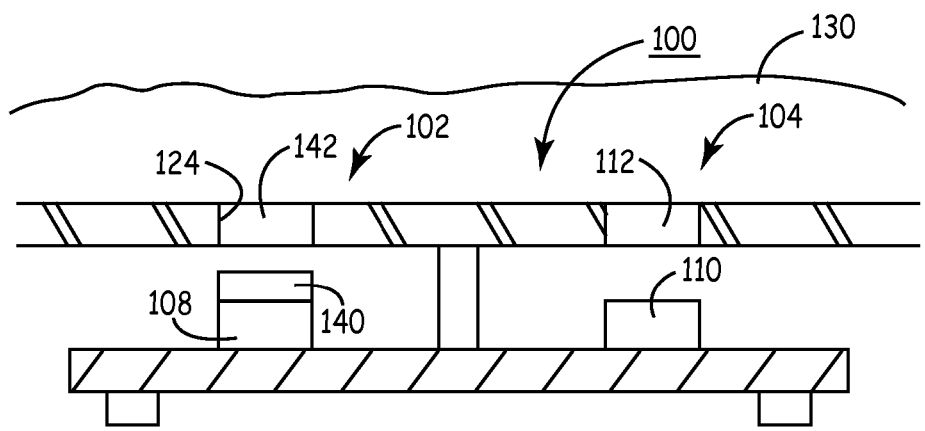
FIG. 3B is a schematic diagram of an alternative embodiment of a TPS.

FIG. 3B is a schematic diagram of an alternative embodiment of a TPS. Light source 108 may be embodied as a white light source and light emitting portion 102 may include a filter 140 for passing selected light wavelengths. In particular, filter 140 may be provided to pass a light wavelength or multiple light wavelengths falling in the blue to ultraviolet light spectrum. Filter 140 may be implemented as a traditional, holographic or other type of light filter and may utilize reflection or absorption light filtration methods. Filter 140 may be a notch filter or bandpass filter passing a limited or wider spectrum of light wavelengths within the blue to ultraviolet light spectrum. Additionally or alternatively, lens 142 may be implemented as a filter for limiting the light wavelengths passed through window 124 to be within the blue to ultraviolet light spectrum. Lens 142 may be a colored lens or implemented as a color filter for passing light corresponding to a selected light wavelength(s). Filter 140, alone or in combination with a filtering lens 142, could be implemented to pass one bandwidth of color, such as blue, or two or more several color bandwidths, such as blue, violet, and ultraviolet. Filter 140 could be include two or more filters in order to obtain a desired filtering profile.

Light detecting component 110 may be implemented as a broad spectrum photodetector for detecting the filtered light emitted by emitting portion 102 and scattered by tissue volume 130 back to detecting portion 104. In this way, TPS 100 selectively senses light in the blue to ultraviolet light spectrum useful in detecting a deoxygenated state of tissue volume 130.

Figure 3C:
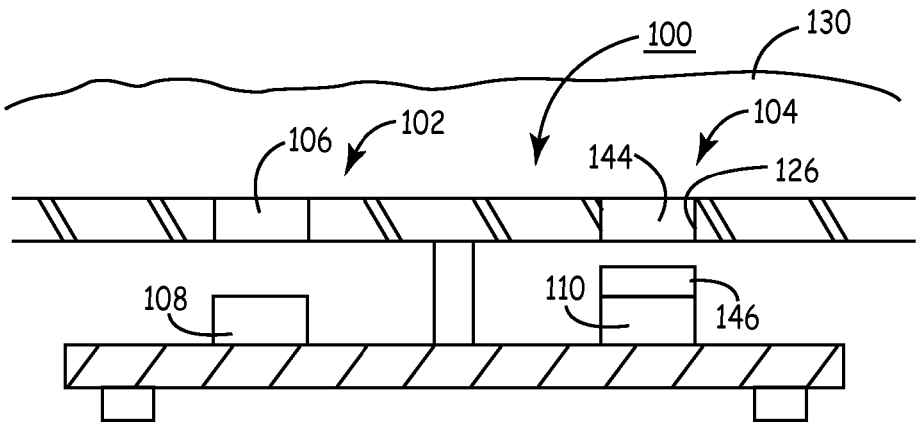
FIG. 3C is a schematic diagram of a TPS including a filter in the light detecting portion.

In FIG. 3C, TPS 100 is shown to include a filter 146 in light detecting portion 104. Light detecting portion may include filter 146 and/or a filtering lens 144 for passing one or multiple light wavelengths falling in the blue to ultraviolet light spectrum. Light source 108 may be implemented as white light or other broad spectrum light source, and light detecting component 110 may be embodied as a broad spectrum photodetector. Filter 146 and/or filtering lens 144 filter the light scattered by tissue volume 130 passing through lens 144 such that only light falling in the blue to ultraviolet light spectrum is received by light detecting component 110.

By providing filtering of either or both of the emitted or received light, TPS 100 can be configured to selectively sense light falling in the blue to ultraviolet light spectrum for use in monitoring perfusion of tissue volume 130. While the operation of TPS 100 is shown with respect to a targeted tissue volume 130 and described as operating in a manner for detecting relative levels of or changes in tissue perfusion, it is recognized that the devices and methods described herein may be adapted for use in monitoring for deoxygenation of a blood volume rather than a tissue volume. As used herein, a "tissue volume" may refer to a volume of blood or body tissue.

Figure 4A:
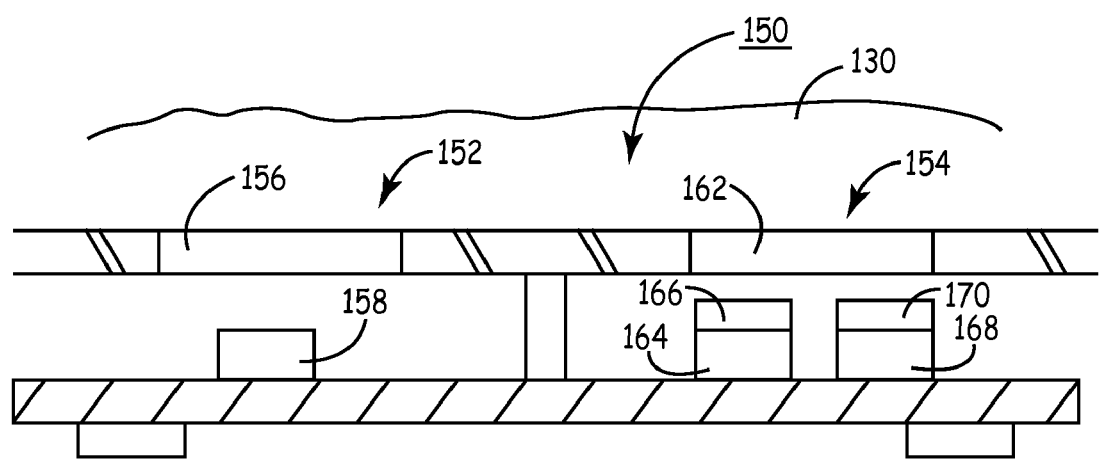
FIG. 4A is a schematic diagram of a TPS according to an alternative embodiment of the present invention.

FIG. 4A is a schematic diagram of a TPS 150 according to an alternative embodiment of the present invention. Light emitting portion 152 includes a broad spectrum light source 158 capable of emitting light in at least two light wavelengths. In one embodiment, the two light wavelengths may correspond to two wavelengths in the blue to ultraviolet light spectrum. In another embodiment, the two light wavelengths may correspond to one wavelength in the blue to ultraviolet light spectrum and another wavelength in the red to infrared light spectrum. In one embodiment, light source 158 is a white light source emitting light in both the blue to ultraviolet light spectrum and the red to infrared light spectrum. Light emitted by source 158 is passed through lens 156 and scattered by tissue volume 130.

Light detecting portion 154 receives scattered light through lens 162 and generates signals corresponding to the detected light. Light detecting portion includes two light detecting components 164 and 168. Light detecting component 164 is provided for detecting blue to ultraviolet light emitted by light source 158. Light detecting component 164 may be embodied as a broad spectrum photodetector provided with a filter 166 for passing only blue to ultraviolet light, or a selected wavelength within the blue to ultraviolet light spectrum, to detecting component 164.

A second light detecting component 168 is provided for detecting red to infrared light emitted by light source 158. Light detecting component 168 may be provided as a broad spectrum photodetector provided with a filter 170 for passing only red to infrared light, or a selected wavelength within the red to infrared light spectrum, to detecting component 168. As such, light detecting components 164 and 168 may be enabled to operate simultaneously to cause TPS 150 to generate simultaneous signals responsive to the intensity of blue to ultraviolet light incident on light detecting portion 154 and the intensity of red to infrared light incident on light detecting portion 154.

As the targeted tissue volume 130 becomes deoxygenated, blue light scattered by tissue volume 130 back to light detecting portion 154 will increase, and red light scattered by tissue volume 130 back to light detecting portion 154 will decrease. Thus, a blue light signal generated by TPS 150 will increase, and a red light signal generated by TPS 150 will decrease. This divergence in blue and red light signals may be used in detecting a state of deoxygenation of the tissue volume 130 as will be described in greater detail below.

Figure 4B:
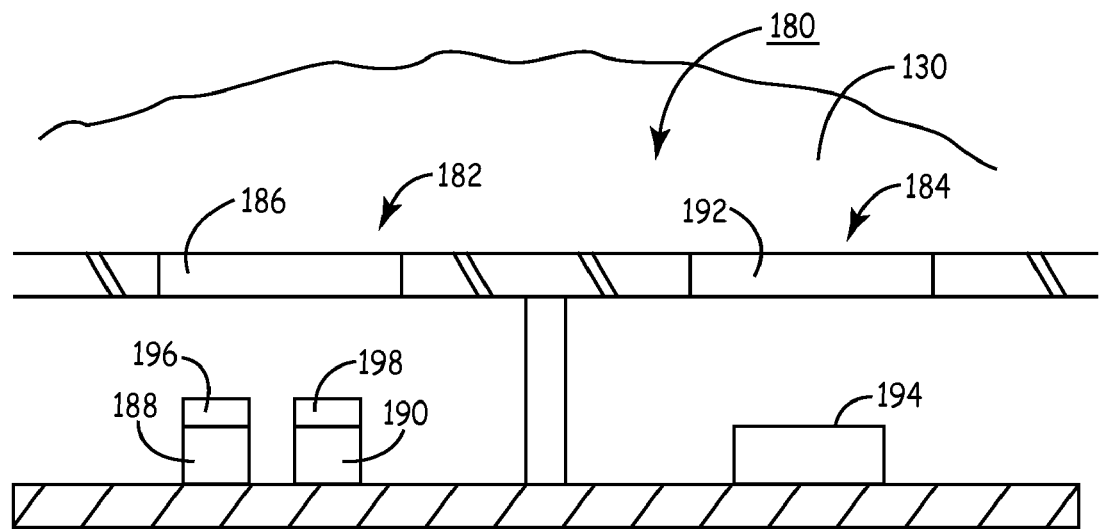
FIG. 4B is a schematic diagram of a TPS includes multiple light sources.

In FIG. 4B, TPS 180 includes multiple light sources 188 and 190 in light emitting portion 182. Light sources 188 and 190 are provided for emitting two different light wavelengths. For example, in one embodiment one light source 188 is provided as a blue LED and the other light source 190 is provided as a red LED. Alternatively, light sources 188 and 190 may emit a spectrum of light wavelengths with filters 196 and 198 provided for limiting the light wavelengths passed through lens 186 to one or more wavelengths in the blue to ultraviolet light spectrum and one or more wavelengths in the red to infrared light spectrum, respectfully.

Light detecting portion 184 includes a light detecting component 194 which detects the emitted light scattered by tissue volume 130 through lens 192. Detecting component 194 may be a broad spectrum photodetector. Light sources 188 and 190 may be enabled in a sequential manner such that detecting component 194 emits a first current signal corresponding to detected blue to ultraviolet light when light source 188 is enabled to emit light and a second current signal corresponding to detected red to infrared light when light source 190 is enabled to emit light.

Figure 4C:
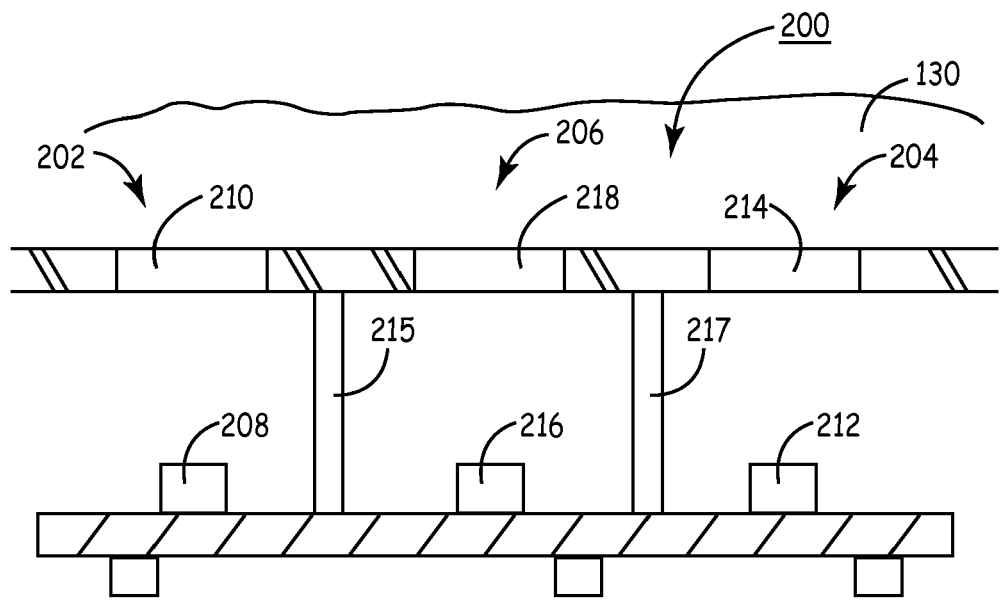
FIG. 4C is a schematic diagram of a TPS including multiple light emitting portions.

FIG. 4C is a diagram of a TPS 200 including multiple emitting portions 202 and 204. In FIG. 4B, light sources 188 and 190 are shown to be included in the same emitting portion 182, each incorporating its own filter 196 and 198, respectively. Alternatively, multiple white light sources 208 and 212 can be configured in two separate emitting portions 202 and 204, each with its own filtering lens 210 and 214, respectively, for passing different selected wavelengths from each of the emitting portions 202 and 204.

Each of the emitting portions 202 and 204 are separated from the light detecting portion 206 by light barriers 215 and 217. A light detecting component 216 generates a signal in response to light passing through lens 218. Light detecting component 216 may be a broad spectrum photodetector for detecting light emitted from both emitting portions 202 and 204 and scattered by tissue 130. In one embodiment, emitting portion 202 emits light in the blue to ultraviolet light spectrum and emitting portion 204 emits light in the red to infrared spectrum. Emitting portions 202 and 204 may be enabled to emit light in sequence to allow photodetector 216 to generate sequential signals responsive to the two different light wavelengths for use in detecting a tissue perfusion state.

Figure 4D:
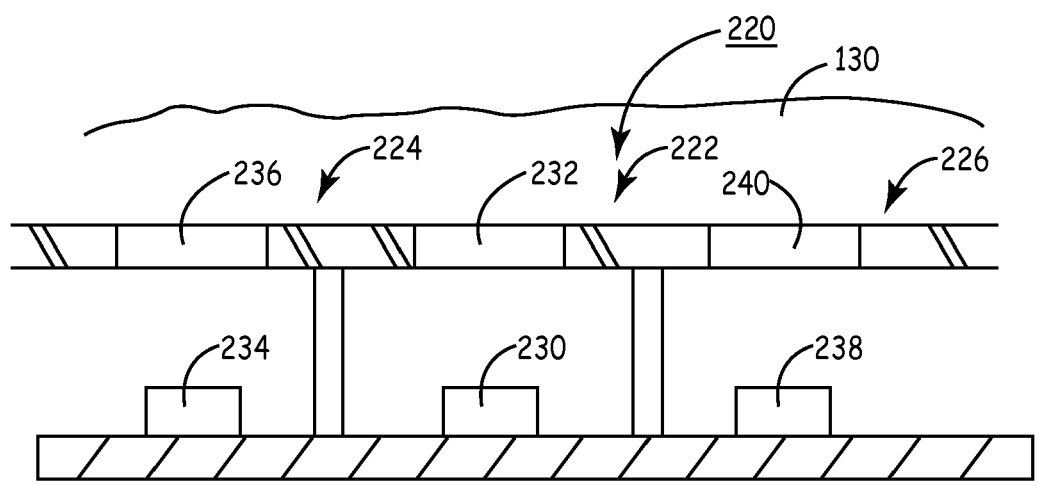
FIG. 4D is a schematic diagram of yet another embodiment of a TPS.

FIG. 4D is a diagram of yet another embodiment of a TPS. TPS 220 includes multiple light detecting portions 224 and 226, each including a light detecting component 234 and 238 receiving light through a filtering lens 236 and 240, respectively. Filtering lenses 236 and 240 pass different light wavelengths such that one detecting portion 224 is configured to detect a first light wavelength, e.g. blue light, and the other detecting portion 226 is configure to detect a second light wavelength different than the first, e.g. red light.

Light emitting portion 222 includes a light source 230 capable of emitting both of the first and second light wavelengths detectable by light detecting portions 224 and 226. Light is emitted through lens 232, which is a non-filtering lens, and is scattered by tissue volume 130 back to the two light detection portions 224 and 226.

It is recognized that a variety of configurations may be conceived for emitting and detecting selected light wavelengths using various combinations of light sources, light detecting components, and filters. A power savings may be realized when a single white light source is used to emit all wavelengths of interest with each wavelength of interest being measured using filtering techniques applied in the light detecting portion(s).

Figure 5:
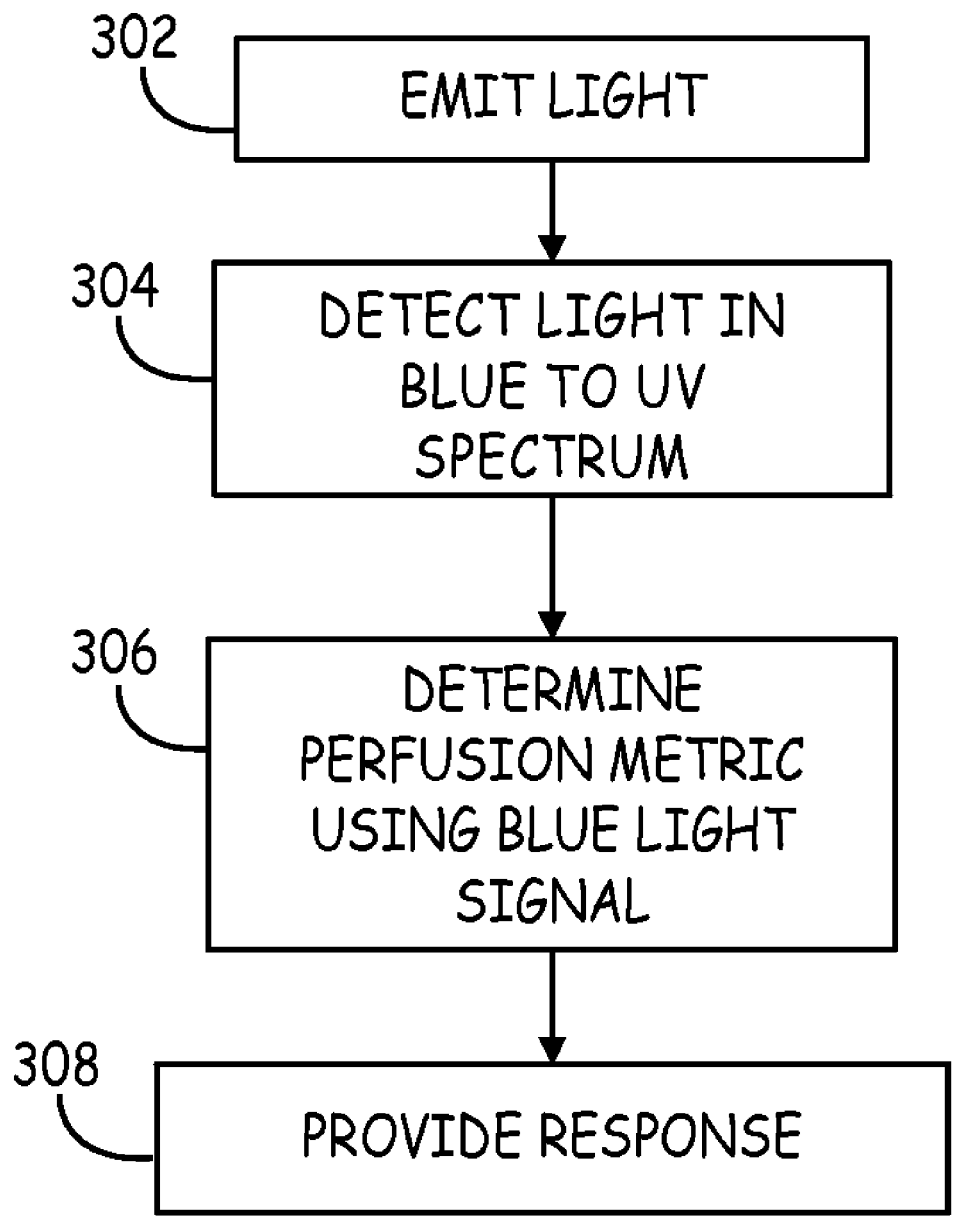
FIG. 5 is a flow chart of a method for monitoring tissue perfusion according to one embodiment of the invention.

FIG. 5 is a flow chart of a method 300 for monitoring tissue perfusion according to one embodiment of the invention. Flow chart 300 and other flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302, light is emitted from a TPS in response to a driver signal delivered to the light emitting portion of the TPS under the control of timing and control circuitry. The emitted light includes a light wavelength falling in the blue to ultraviolet light spectrum. The emitted light may be a narrow band spectrum or a targeted wavelength, e.g. from a blue LED or a filtered white light, or the emitted light may be a broad spectrum of wavelengths, e.g. from a non-filtered white light source. A "white light" source can contain a broad continuous range of wavelengths (like light from a light bulb) or the white light source can be a light source that appears white to the eye but is actually a set of various wavelengths that produce perceived white light (like light from a white LED).

At block 304, the emitted light wavelength falling in the blue to ultraviolet (UV) light spectrum is detected by a light detector. One or more light wavelengths may be detected. The light detector generates a signal responsive to at least one wavelength falling in the blue to ultraviolet light spectrum. At block 306 the light detector signal is used by processing circuitry to determine a metric of tissue perfusion. The metric may determined as a time interval for an integrated current signal to reach a predetermined limit, a relative change in a measured time interval, the amplitude of the integrated current signal at a fixed time interval, or a relative change in the integrated current signal amplitude at the fixed time interval.

In an alternative embodiment, ultraviolet light is emitted and fluorescence of the tissue is measured by the light detecting portion. The light detector would detect light in the visible and/or invisible range and be responsive to one or more selected wavelengths or color bands based on detector characteristics and/or implemented light filter(s).

The measured blue light signal is used by an implantable medical device to provide a response at block 308. Depending on the determined perfusion metric, no action may be taken, the perfusion metric data may be stored, or a therapy and/or arrhythmia detection parameters may be adjusted or delivered.

Figure 6:
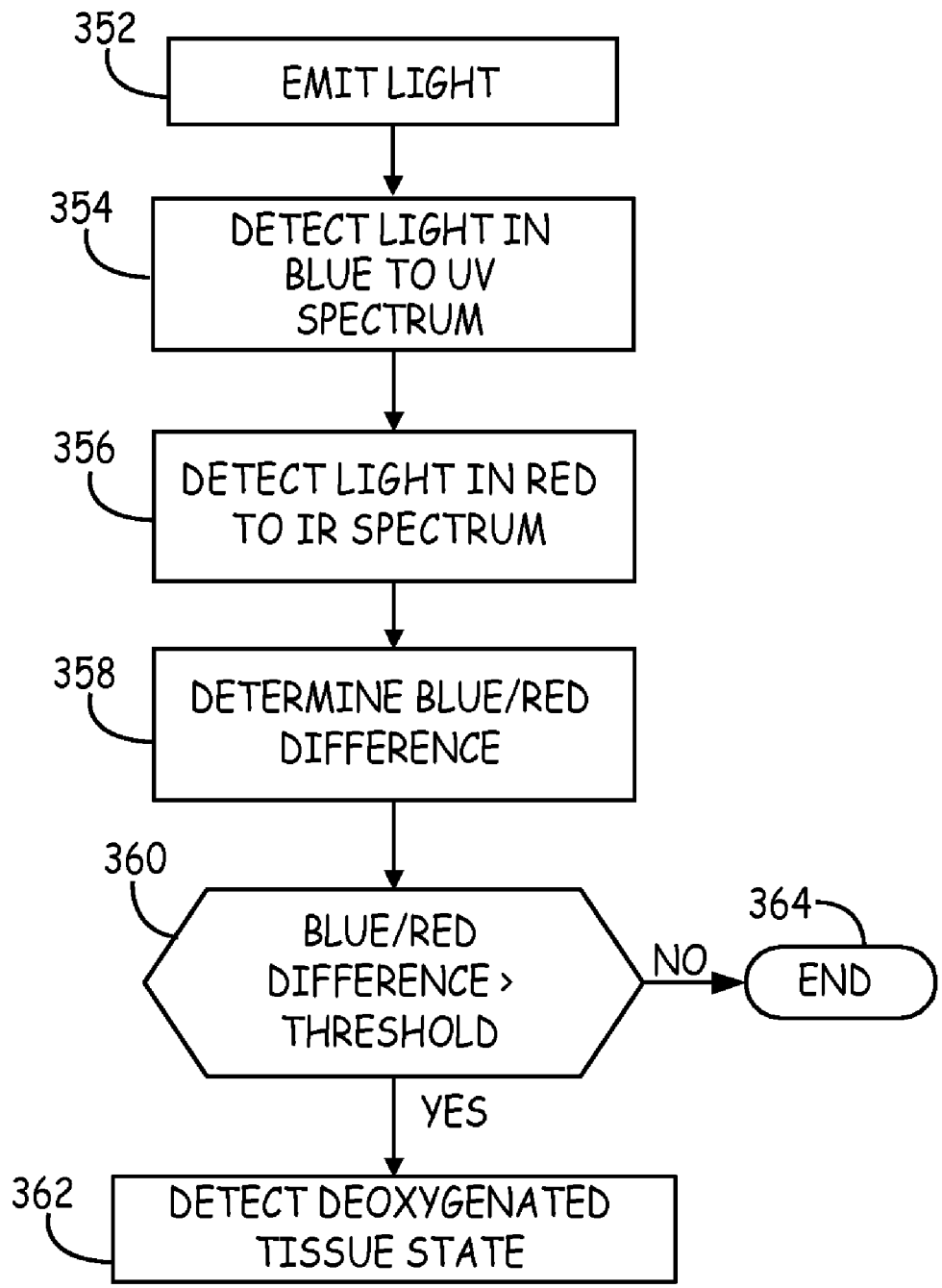
FIG. 6 is a flow chart of another method for monitoring tissue perfusion.

FIG. 6 is a flow chart of another method 350 for monitoring tissue perfusion. At block 352, light is emitted by one or more light emitting portions of a TPS. The emitted light includes at least one wavelength falling in the blue to ultraviolet light spectrum and at least one wavelength in the red to infrared light spectrum. As described above, any configuration of narrow-spectrum or specific wavelength light sources and/or filtered light emitting portions may be implemented for emitting the two different wavelengths. Alternatively a white light source is used.

At block 354, a light detecting portion of the TPS is enabled to detect the first light wavelength falling in the blue to ultraviolet light spectrum and scattered by a targeted tissue volume. At block 356, the same or a different light detecting portion of the TPS is enabled to detect the second light wavelength falling in the red to infrared light spectrum. Detection of the two different light wavelengths may occur simultaneously or sequentially depending upon the configuration of the light emitting and light detecting portions of the TPS.

At block 358 a difference between or ratio of the two detected light wavelengths is determined. As tissue becomes more deoxygenated, a blue light signal will increase and a red light signal will decrease. As such, a difference or divergence of these signals may be used in monitoring tissue perfusion. At block 360, the computed difference or ratio is compared to a threshold. If the difference or ratio exceeds a predefined threshold, a deoxygenated state of the targeted tissue volume is detected at block 362. If the threshold is not exceeded, method 350 is terminated at block 364. It is contemplated that various levels of thresholds may be defined to enable detection of varying states of tissue deoxygenation. The difference or ratio computed at block 358 may be a difference between any wavelength falling in the blue to ultraviolet light spectrum and any wavelength falling in the red to infrared light spectrum.

Figure 7:
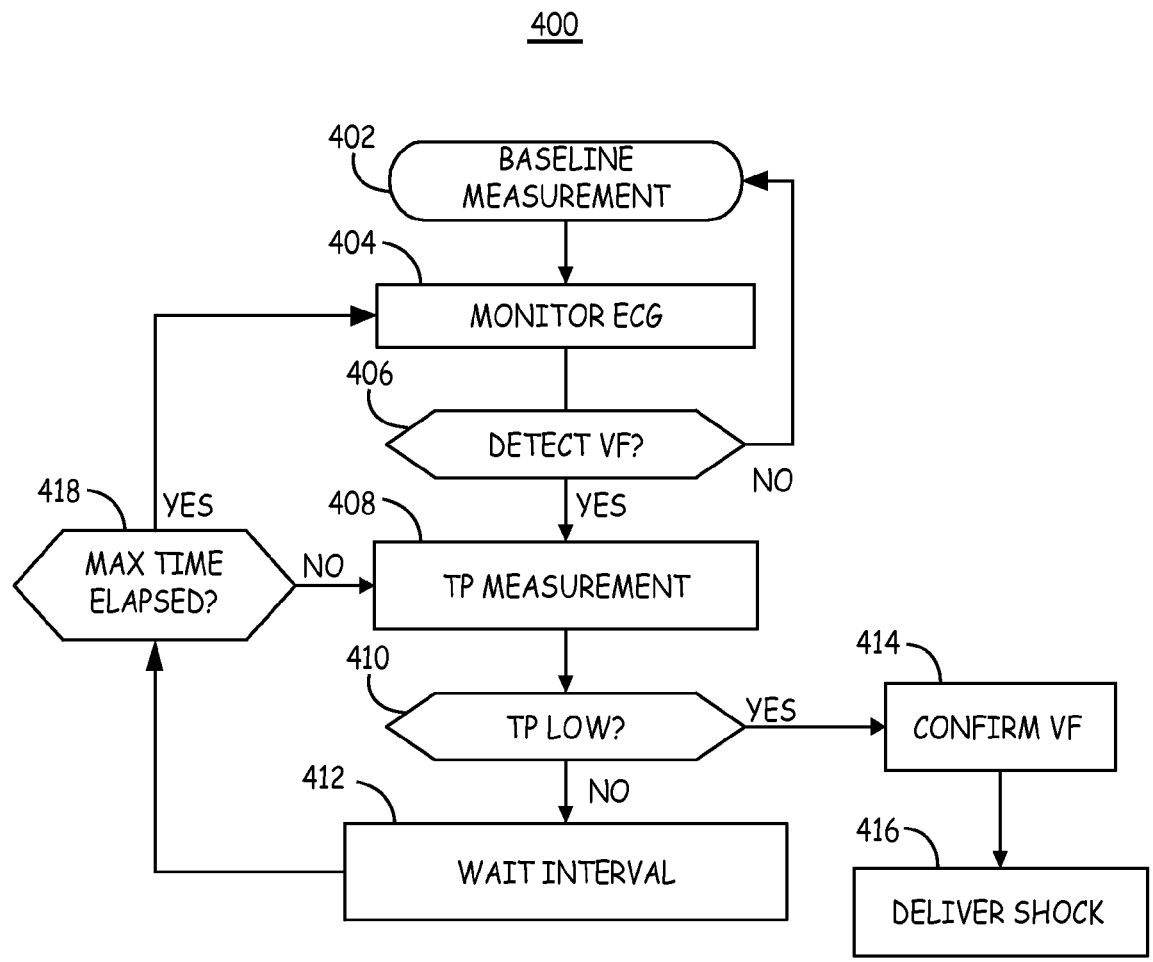
FIG. 7 is a flow chart of a tissue perfusion monitoring method for use in an ICD.

FIG. 7 is a flow chart of a tissue perfusion monitoring method for use in an ICD. Method 400 employs a method of detecting a state of tissue perfusion for confirming a need for delivery of a defibrillation shock. Method 400 may be used, for example, in a SubQ ICD when low amplitude fibrillation signals become more difficult to detect using subcutaneously implanted electrodes. At block 402, a baseline tissue perfusion measurement may be made. A baseline measurement is optional depending on the measurement methods used. A TPS may be pre-calibrated such that baseline comparisons are not needed. Alternatively, a series of measurements may be made during a suspected physiological event to detect a worsening state of tissue perfusion with relative comparisons between sequential measurements being made rather than comparisons to a pre-event baseline measurement.

The perfusion measurements used in method 400 include detecting a signal generated by a TPS corresponding to at least one wavelength in the blue to ultraviolet light spectrum. The perfusion measurements may include other light detection, for example detecting a wavelength in the red to infrared spectrum as described in conjunction with FIG. 6.

At block 404, subcutaneous ECG or intracardiac EGM signals are monitored using available sensing electrodes. The cardiac electrical signals are evaluated for detecting cardiac arrhythmias. If an arrhythmia, such as ventricular fibrillation (VF) is detected, as determined at block 406, tissue perfusion (TP) monitoring is initiated at block 408. A tissue perfusion measurement may be performed at block 408 and compared to the baseline measurement or a predetermined threshold to determine if tissue perfusion is significantly decreased at block 410.

Alternatively, tissue perfusion measurements are repeated at predetermined intervals beginning after the VF detection to determine if a decreasing state of tissue perfusion is occurring. Detection of a decreasing state of tissue perfusion can be used to confirm the VF detection and the need for delivering a therapy. At block 412, method 400 waits a predetermined time interval after making the first measurement, for example 20 to 40 seconds. If a maximum time interval has elapsed, for example 2 to 5 minutes, or a maximum number of perfusion measurements have been made, as determined at block 418, method 400 returns to block 404 to continue monitoring the ECG/EGM. A decreased state of tissue perfusion is not detected.

If the maximum time interval has not elapsed, another tissue perfusion measurement is made at block 408. The new tissue perfusion measurement is compared to the previous measurement at block 410 to determine if tissue perfusion has significantly decreased. If not, method 400 waits another predetermined interval and repeats steps 408 through 412 until a state of decreased tissue perfusion is detected or until the maximum monitoring time has elapsed. If a state of decreased tissue perfusion is detected, the arrhythmia detection is confirmed at block 414 and a therapy is delivered at block 416.

Figure 8:
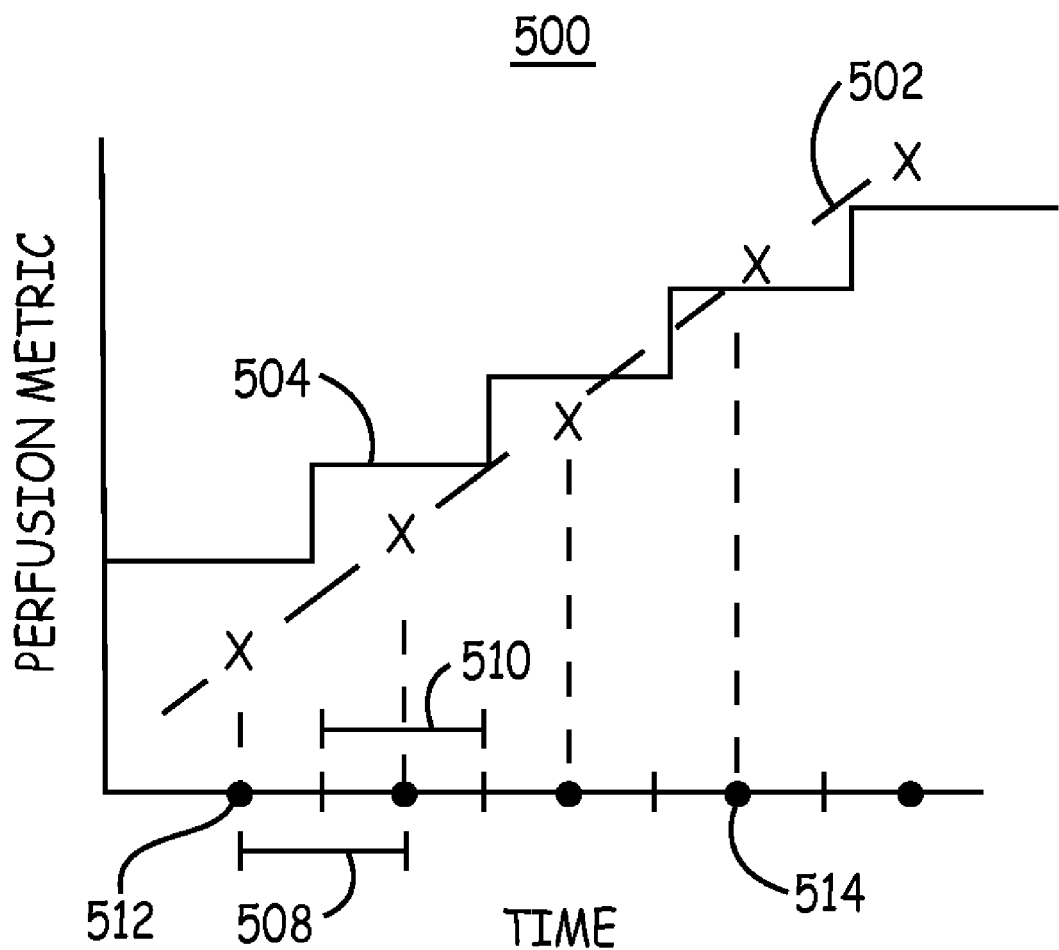
FIG. 8 is a graph of the divergence between a blue light and a red light signal used in monitoring tissue perfusion.

FIG. 8 is a graph of the divergence between a blue light and a red light signal used in monitoring tissue perfusion. The divergence 502, indicated by X's, between the red and blue light signals is measured as a metric of tissue perfusion (y-axis). The divergence 502 is measured at regular intervals 508 beginning at time point 512, which may correspond to the time of an arrhythmia detection, such as a VF detection. Each divergence measurement 502 is compared to a time-dependent threshold 504 to determine if a significant change in tissue perfusion has occurred. Alternatively the difference between successive divergence measurement may be compared to a time-dependent threshold.

The time-dependent threshold 504 is shown as a step-wise threshold that increases at regular time intervals 510. The divergence 502 measured at time point 514 exceeds the time-dependent threshold 504. Accordingly, at time 514, a significant decrease in tissue perfusion is detected which may be used to trigger a therapy and/or confirm a detected physiological event. In alternative embodiments, time-dependent threshold 504 may be defined as any linear or non-linear function of time rather than the step-wise threshold shown in FIG. 8. By providing a time-dependent threshold, an expected decrease in perfusion since the onset of a clinical event can be compared to an actual change in measured perfusion to determine if the measured trend in tissue perfusion corresponds to a trend expected to occur during or after a physiological event, such as ventricular fibrillation.

Thus, a device and associated methods for monitoring tissue perfusion have been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
a light source emitting light comprising a first light wavelength corresponding to a blue to ultraviolet light spectrum and a second wavelength corresponding to a red to infrared light spectrum;
a light detector receiving light emitted by the light source and scattered by a volume of body tissue, the light detector emitting a first signal correlated to the received light having the first light wavelength and a second signal correlated to the received light having the second wavelength;
a processor configured to:
receive the first signal and the second signal from the light detector;
determine a divergence between the first signal and the second signal; and
determine patient condition in response to the divergence; and
further comprising an electrode for sensing cardiac electrical signals, wherein the processor receives the cardiac electrical signals and detects a heart rhythm in response to the cardiac electrical signals, and wherein the processor determines the patient condition further based at least in part, on the heart rhythm.

2. The device of claim 1, further comprising:
a therapy delivery module; and
a control module coupled to the processor and the therapy delivery module, the control module causing the therapy delivery module to deliver a therapy in response to the determined patient condition, wherein the patient condition is ventricular fibrillation and the therapy is a defibrillation therapy.

3. The device of claim 1 wherein the light source comprises a white light source.

4. The device of claim 3 further comprising a filter passing the first light wavelength to the light detector.

5. The device of claim 4 wherein the filter filters the emitted light.

6. The device of claim 4 wherein the filter filters the light received by the light detector after being scattered by the body tissue volume.

7. The device of claim 3 wherein the filter comprises a lens through which one of the emitted light and the received light passes.

8. The device of claim 1 wherein the light detector detects fluorescence of the body tissue in response to the first light wavelength corresponding to ultraviolet light.

9. The device of claim 2 wherein the processor determines the patient condition at predetermined time intervals subsequent to detecting the heart rhythm.

10. The device of claim 9 wherein determining the patient condition further comprises comparing the determined patient condition to a time-dependent threshold and wherein the patient control module causes the therapy delivery module to deliver a therapy in response to the determined patient condition reaching a time-dependent threshold.

11. An implantable medical device, comprising:
an electrode sensing a cardiac electrical signal;
a light source emitting light comprising a first light wavelength corresponding to a blue to ultraviolet light spectrum and a second light wavelength corresponding to a red to infrared light spectrum;
a light detector receiving light emitted by the light source, the light detector comprising a first filtered photodetector selectively detecting light corresponding to the first light wavelength and a second filtered photodetector selectively detecting light corresponding to the second light wavelength, the light detector emitting a first signal correlated to the received light having the first light wavelength and a second signal correlated to the received light having the second light wavelength;
a processor receiving the cardiac electrical signal, detecting an arrhythmia in response to the cardiac electrical signal, receiving the first signal and the second signal from the light detector, determining a divergence between the first light signal and the second light signal at predetermined time intervals following detecting the arrhythmia, comparing the divergence to a predetermined time-dependent threshold, and confirming the arrhythmia in response to the comparison; and
a therapy control module coupled to the processor and delivering an anti-arrhythmia therapy in response to the arrhythmia confirmation.

12. A method for monitoring a physiological condition for use in an implantable medical device, comprising:
emitting light comprising a first light wavelength corresponding to a blue to ultraviolet light spectrum from a light source;
detecting light having the first light wavelength and scattered by a volume of body tissue, and emitting a first signal correlated to the detected light having the first light wavelength;
emitting a second light wavelength corresponding to a red to infrared light spectrum;
detecting light comprising the second light wavelength and scattered by the body tissue volume, and emitting a second signal correlated to the detected light comprising the second light wavelength;
determining a patient condition in response to the first signal and the second signal by determining a divergence between the first signal and the second signal sensing cardiac electrical signals; and
detecting a heart rhythm in response to the sensed cardiac electrical signals;
wherein the determining the patient condition step is further based, at least in part, on the heart rhythm.

13. The method of claim 12 further comprising filtering one of the emitted light and the detected light.

14. The method of claim 12 wherein the first light wavelength corresponds to ultraviolet light and detecting the first light wavelength comprises detecting fluorescence of the body tissue volume.

15. The method of claim 12 wherein the processor determines the patient condition at predetermined time intervals subsequent to detecting the heart rhythm.

16. The method of claim 15 wherein determining the patient condition further comprises comparing the determined patient condition to a time-dependent threshold.

* * * * *